(12) United States Patent
Kato et al.

(10) Patent No.: US 7,833,726 B2
(45) Date of Patent: Nov. 16, 2010

(54) ANTIBODY FOR ASSAYING ADAMTS13 ACTIVITY AND METHOD FOR ASSAYING THE ACTIVITY

(75) Inventors: Seiji Kato, Kyoto (JP); Hisahide Hiura, Kyoto (JP); Yoshihiro Fujimura, Nara (JP); Masanori Matsumoto, Kashihara (JP)

(73) Assignee: Alfresa Pharma Corporation, Osaka (JP)

( * ) Notice: Subject to any disclaimer, the term of this patent is extended or adjusted under 35 U.S.C. 154(b) by 372 days.

(21) Appl. No.: 11/816,168

(22) PCT Filed: Jan. 26, 2006

(86) PCT No.: PCT/JP2006/301231
§ 371 (c)(1),
(2), (4) Date: Aug. 13, 2007

(87) PCT Pub. No.: WO2006/085441
PCT Pub. Date: Aug. 17, 2006

(65) Prior Publication Data
US 2009/0142776 A1 Jun. 4, 2009

(30) Foreign Application Priority Data
Feb. 14, 2005 (JP) .............................. 2005-036612
May 30, 2005 (JP) .............................. 2005-157530

(51) Int. Cl.
*C07K 16/00* (2006.01)
*C12N 5/20* (2006.01)
*G01N 33/53* (2006.01)

(52) U.S. Cl. ..................... 435/7.1; 530/387.9; 435/326; 435/810

(58) Field of Classification Search ........................ None
See application file for complete search history.

(56) References Cited

U.S. PATENT DOCUMENTS

| | | | | |
|---|---|---|---|---|
| 4,281,061 A * | 7/1981 | Zuk et al. | ..................... | 435/7.9 |
| 7,112,666 B2 * | 9/2006 | Soejima et al. | ............. | 536/23.2 |
| 2005/0051428 A1 * | 3/2005 | Gabriel | ........................ | 204/452 |
| 2007/0065895 A1 | 3/2007 | Miyata et al. | | |

FOREIGN PATENT DOCUMENTS

WO WO 2004/035778 A1 4/2004
WO WO 2005/008241 A1 1/2005

OTHER PUBLICATIONS

Dent et al. Identification of a cleavage site directing the immunochemical detection of molecular abnormalities in type IIA von Willebrand factor. Proc. Nati. Acad. Sci. USA vol. 87, pp. 6306-6310, Aug. 1990.*

Mort et al. The use of cleavage site specific antibodies to delineate protein processing and breakdown pathways. Mol Pathol. Feb. 1999;52(1):11-8.*

Kato, Seiji, et al., "Monoclonal Antibodies to a VWF-A2 Decapeptide with the C-Terminal Residue Tyr 1605, Generated by ADAMTS13 Cleavage, Develop a Highly Sensitive ELISA for Its Activity and Characterize Upsawh-Schulman Syndrome," Blood, 2005, 106: Abstract 2643.

Kato, Seiji, et al., "Novel monoclonal antibody-based enzyme immunoassay for determining plasma levels of ADAMTS13 activity," Transfusion, Aug. 2006, 46:1444-1452.

Kokame, Koichi, et al., "VWF73, a region from D1596 to R1668 of von Willebrand factor, provides a minimal substrate for ADAMTS-13," Blood. Jan. 15, 2004, 103(2):607-612.

Zhou, Wenhua and Tsai, Han-Mou, "An enzyme immunoassay of ADAMTS13 distinguishes patients with thrombotic thrombocytopenic purpura from normal individuals and carriers of ADAMTS13 mutations," Thromb Haemost, 2004, 91:806-11.

Furlan, "Von Willebrand Factor—Cleaving Protease in Thrombotic Thrombocytopenic Purpura and the Hemolytic-Uremic Syndrome" New Engl. J. of Medicine, vol. 339, No. 22, pp. 1578-1564 (1998).

Tsai et al. "Antibodies to Von Willebrand Factor—Cleaving Protease in Acute Thrombotic Thrombocytopenic Purpura" New Engl. J. of Medicine, vol. 339, No. 22, pp. 1585-1594.

Kinoshita et al, "Upshaw—Schulman Syndrome Revisited: A Concept of Congenital Thrombotic Thrombocytopenic Purpura" International Journal of Hematology, vol. 74, pp. 101-108 (2001).

Soejima et al. "A Novel Human Metalloprotease Synthesized in the Liver and Secreted into the Blood: Possibly, the von Willebrand Factor-Cleaving Protease?" The Journal of Biochemistry, vol. 130, No. 4, pp. 475-480 (2001).

Zheng et al. "Structure of von Willebrand Factor-cleaving Protease: (AAMTS13), a Metalloprotease Involved in Thrombotic Thrombocytopenic Purpura" The Journal of Biological Chemistry, vol. 276, No. 44, pp. 41059-41063.

Kokame et al. "VWF73, a region from D1596 to R1668 of von Willebrand factor, provides a minimal substrate for ADAMTS-13" Blood, vol. 103 No. 2, Jan. 15, 2004.

Whitelock et al. "ADAMTS-13 activity in plasma is rapidly measured by a new ELISA method that uses recombinant VWF-A2 domain as substrate" Journal of Thrombosis and Haemostasis, vol. 2; 465-491 (2004).

*Primary Examiner*—Maher M Haddad
(74) *Attorney, Agent, or Firm*—Joseph Hyosuk Kim; JHK Law

(57) ABSTRACT

The subject of the present invention is to provide a useful antibody for measuring ADAMTS13 activity, in particular, a monoclonal antibody and a method for measuring ADAMTS13 activity. Further, another subject of the present invention also is to provide a monoclonal antibody which has specific reactivity to an antigenic determinant site produced by reacting ADAMTS13 with VWF that is a substrate or a partial peptide of VWF that is a potential substrate, but has no specific reactivity to the complete VWF molecule, and a use of the antibody of interest. Those subjects were achieved by succeeding in obtaining a monoclonal antibody (anti-N-10 monoclonal antibody) which has specific reactivity to a cleavage site that is cleavable by ADAMTS13 in the partial peptide of VWF, and further by finding a method for measuring ADAMTS13 activity using the monoclonal antibody of interest.

14 Claims, 1 Drawing Sheet

OTHER PUBLICATIONS

Zhou et al. "An enzyme immunoassay of ADAMTS13 distinguishes patients with thrombotic thrombocytopenic purpura from normal individuals and carriers of ADAMTS13 mutations" Thrombosis and Haemostasis, vol. 91, No. 4, pp. 806-811 (2004).

Japanese Journal of Thrombosis and Hemostasis vol. 15 (2004) English Translation.

Ooumi, Shinobu. "Cell technology Separate Volume Jikken Protocol Series New Edition Ant-peptide Kotai Jikken Protocol—Idenshi Sanbutsu no Dotei kara Tanpakushitsu Kono Kaiseiki made—", Shujunsha Co., Ltd., pp. 130-143 (2004) English Translation.

\* cited by examiner

SEQUENCE LISTING

```
<160> NUMBER OF SEQ ID NOS: 12

<210> SEQ ID NO 1
<211> LENGTH: 73
<212> TYPE: PRT
<213> ORGANISM: Artificial
<220> FEATURE:
<223> OTHER INFORMATION: VWF peptide cleaved by ADAMTS13
<220> FEATURE:
<221> NAME/KEY: PEPTIDE
<222> LOCATION: (1)..(73)
<223> OTHER INFORMATION:

<400> SEQUENCE: 1

Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70

<210> SEQ ID NO 2
<211> LENGTH: 10
<212> TYPE: PRT
<213> ORGANISM: Artificial
<220> FEATURE:
<223> OTHER INFORMATION: N-terminal peptide (10AA) of VWF73

<400> SEQUENCE: 2

Asp Arg Glu Gln Ala Pro Asn Leu Val Tyr
1               5                   10

<210> SEQ ID NO 3
<211> LENGTH: 6
<212> TYPE: PRT
<213> ORGANISM: Artificial
<220> FEATURE:
<223> OTHER INFORMATION: N-terminal peptide (6AA)of VWF73

<400> SEQUENCE: 3

Asp Arg Glu Gln Ala Pro
1               5

<210> SEQ ID NO 4
<211> LENGTH: 8
<212> TYPE: PRT
```

```
<213> ORGANISM: Artificial
<220> FEATURE:
<223> OTHER INFORMATION: N-terminal peptide (8AA) of VWF73

<400> SEQUENCE: 4

Asp Arg Glu Gln Ala Pro Asn Leu
1               5

<210> SEQ ID NO 5
<211> LENGTH: 11
<212> TYPE: PRT
<213> ORGANISM: Artificial
<220> FEATURE:
<223> OTHER INFORMATION: N-terminal peptide (11AA) of VWF73

<400> SEQUENCE: 5

Asp Arg Glu Gln Ala Pro Asn Leu Val Tyr Met
1               5                   10

<210> SEQ ID NO 6
<211> LENGTH: 9
<212> TYPE: PRT
<213> ORGANISM: Artificial
<220> FEATURE:
<223> OTHER INFORMATION: N-terminal peptide (9AA) of VWF73

<400> SEQUENCE: 6

Asp Arg Glu Gln Ala Pro Asn Leu Val
1               5

<210> SEQ ID NO 7
<211> LENGTH: 13
<212> TYPE: PRT
<213> ORGANISM: Artificial
<220> FEATURE:
<223> OTHER INFORMATION: N-terminal peptide (13AA) of VWF73

<400> SEQUENCE: 7

Asp Arg Glu Gln Ala Pro Asn Leu Val Tyr Met Val Thr
1               5                   10

<210> SEQ ID NO 8
<211> LENGTH: 15
<212> TYPE: PRT
<213> ORGANISM: Artificial
<220> FEATURE:
<223> OTHER INFORMATION: N-terminal peptide (15 AA) of VWF73

<400> SEQUENCE: 8

Asp Arg Glu Gln Ala Pro Asn Leu Val Tyr Met Val Thr Gly Asn
1               5                   10                  15

<210> SEQ ID NO 9
<211> LENGTH: 4
<212> TYPE: PRT
<213> ORGANISM: Artificial
<220> FEATURE:
<223> OTHER INFORMATION: N-10 C-terminal peptide sequence
<220> FEATURE:
<221> NAME/KEY: PEPTIDE
<222> LOCATION: (1)..(4)
<223> OTHER INFORMATION:

<400> SEQUENCE: 9

Asn Leu Val Tyr
1
```

```
<210> SEQ ID NO 10
<211> LENGTH: 10
<212> TYPE: PRT
<213> ORGANISM: Artificial
<220> FEATURE:
<223> OTHER INFORMATION: VWF Cleaving peptide C-terminal region

<400> SEQUENCE: 10

Met Val Thr Gly Asn Pro Ala Ser Asp Glu
1               5                   10

<210> SEQ ID NO 11
<211> LENGTH: 15
<212> TYPE: PRT
<213> ORGANISM: Artificial
<220> FEATURE:
<223> OTHER INFORMATION: C-15 peptide including ADAMTS 13 cleaving site

<400> SEQUENCE: 11

Pro Asn Leu Val Tyr Met Val Thr Gly Asn Pro Ala Ser Asp Glu
1               5                   10                  15

<210> SEQ ID NO 12
<211> LENGTH: 4
<212> TYPE: PRT
<213> ORGANISM: Artificial
<220> FEATURE:
<223> OTHER INFORMATION: N-terminal peptide of C-10

<400> SEQUENCE: 12

Met Val Thr Gly
1
```

ANTIBODY FOR ASSAYING ADAMTS13 ACTIVITY AND METHOD FOR ASSAYING THE ACTIVITY

TECHNICAL FIELD

The present invention relates to an antibody, in particular, a monoclonal antibody, which has the specific reactivity (affinity) to an antigenic determinant site produced by reacting a VWF-cleavage enzyme (hereinafter referred to as "ADAMTS13") with a Von Willebrand factor (hereinafter sometimes referred to as "VWF") or a peptide 1 having the amino acid sequence represented by SEQ ID NO: given in the sequence listing, but does not have a significant specific reactivity to the VWF or the peptide with no affection given by ADAMTS13; a method for producing the same; and a use thereof.

This application claims the priority of Japanese Patent Application Nos. 2005-036612 and 2005-157530, which are incorporated herein by reference.

BACKGROUND ART

Thrombotic thrombocytopenic purpura (TTP) is a syndrome characterized by, for example, thrombocytopenia, hemolytic anemia and perturbing neurological dysfunction. It was formerly a poor prognostic disease with approximately 80% of patients died within 3 months. However, currently, the prognosis has considerably improved by plasma exchange.

Recently, it was reported that TTP might be attributed to the decrease in activity of VWF-cleaving enzyme (ADAMTS13). Namely, it has been revealed that an IgG type inhibitor against VWF-cleaving enzyme is produced to decrease the enzyme activity, causing the acquired TTP (Non-patent Document Nos. 1 and 2). Further, Upshaw-Schulman syndrome (USS) which is congenital TTP was proved to be genetically deficient in VWF-cleaving enzyme (Non-patent Document No. 3). The gene encoding this VWF-cleaving enzyme was proved to be ADAMTS13 (Non-patent Document Nos. 4 and 5).

ADAMTS13 is a zinc metalloprotease and specifically cleaves VWF subunit at Tyr842-Met843 bond. The activity of this enzyme is measured by VWF multimer analysis in which VWF is employed as a substrate to detect the produced VWF fragments by electrophoresis. Since this method has a merit to allow accurate measurement of ADMATS13 activity, but is accompanied with complicated operation, it has been desired to develop an especially simpler measuring method.

Non-patent Documents Nos. 6 to 8 report a method wherein the A2 domain in VWF or a fraction thereof is used a substrate for ADAMTS13 to measure ADAMTS13 activity. They are not natural substrates, but expressed in *E. coli* by genetic recombination. Based on the fact that these substrates are degraded by ADAMTS13 present in plasma samples, the measuring methods described above detect these substrates in molecular weight by electrophoresis and Western blotting, and then react these substrates with the enzyme to measure immunologically the remaining undegraded substrates, thereby to detect and determine ADAMTS13 activity. However, since these methods use a reverse correlation between the ADAMTS13 activity and the observed signal intensity with the standard curve taking a negative gradient, a problem remains to be solved that these method are not able to provide satisfactory sensitivity and reproducibility within a clinically important region of as low as 5% or below.

To improve this problem, a method for measuring ADAMTS13 activity of plasma using a quenchable fluorescent substrate has been reported (Non-patent Document No. 9). This method contains a standard curve taking a positive gradient where fluorescence intensity increases as ADAMTS13 activity increases. However, the method has a problem for use in a general clinical laboratory, because it must use a specially chemically synthesized and expensive substrate to conduct a rate assay by a fluorometer.

[Non-patent Document No. 1] New Engl. J. Med. 339, 1578-1584, 1998

[Non-patent Document No. 2] New Engl. J. Med. 339, 1585-1594, 1988

[Non-patent Document No. 3] J. Hematol. 74, 101-108, 2001

[Non-patent Document No. 4] J. Biochem. 130, 475-480, 2001

[Non-patent Document No. 5] J. Biol. Chem. 276, 41059-41063, 2001

[Non-patent Document No. 6] Blood, 103,607-612, 2004

[Non-patent Document No. 7] J. Thromb. Haemost. 2, 485-491, 2004

[Non-patent Document No. 8] Thromb Haemost. 91, 806-811, 2004

[Non-patent Document No. 9] The Journal of Japanese Society on Thrombosis and Hemostasis, 15,421, 2004

DISCLOSURE OF THE INVENTION

Problems to be Solved

An object of the present invention is to provide a useful antibody for measuring ADAMTS13 activity. In more specifically, the object of the present is to provide an antibody having an affinity for a peptide produced by hydrolyzing VWF, which is a substrate, or the partial peptide of VWF, which can serve as a substrate, with ADAMTS13, a use of the antibody of interest and the antibody of interest in the form of a monoclonal antibody. Further, another object of the present invention is to provide a hybridoma cell line producing the monoclonal antibody of interest.

Means to Solve the Problems

The present inventors strenuously studied to find a method for measuring ADAMTS13 activity and as a result, succeeded in an attempt that a peptide, which had on the C-terminal side an amino acid sequence on the N-terminal side in relation to an ADAMTS13-specific cleavage site in the VWF or the partial peptide thereof to use as a substrate, was used as an antigen to produce a monoclonal antibody which could recognize specifically an antigenic determinant site produced by cleaving the substrate with ADAMTS13, thereby establishing a hybridoma cell line producing the monoclonal antibody of interest and further finding out a use of the monoclonal antibody of interest.

In summary, the present invention is composed of the following:

1. An antibody which has the specific reactivity (affinity) to an antigenic determinant site produced by reacting a VWF-cleavage enzyme (ADAMTS13) with a Von Willebrand factor (VWF) or a peptide having the amino acid sequence represented by SEQ ID NO: 1 given in the sequence listing, but does not have significantly specific reactivity to the peptide having VWF or the amino acid sequence represented by SEQ ID NO: 1 given in the sequence listing.

2. The antibody according to the preceding aspect 1, wherein the antigenic determinant site produced by reacting ADAMTS13 with the VWF or the peptide having the amino acid sequence represented by SEQ ID NO: 1 given in the sequence listing is an antigenic determinant site produced by cleaving the VWF or the peptide with ADAMTS13.

3. The antibody according to the preceding aspect 1 or 2, wherein the antigenic determinant site is present in a new peptide fragment toward the N-terminal side or the C-terminal side from a cleavage site produced by cleaving VWF or the peptide with ADAMTS13.

4. The antibody according to any one of the preceding aspects 1 to 3, wherein the antibody has reactivity to the peptide represented by SEQ ID NO: 2 given in the sequence listing.

5. The antibody according to any one of the preceding aspects 1 to 4, wherein the antibody has reactivity to a domain comprising at least 4 amino acid residues from the C-terminus of the peptide represented by SEQ ID NO: 2 given in the sequence listing.

6. The antibody according to any one of the preceding aspects 1 to 5, wherein the antibody has reactivity to the peptide represented by SEQ ID NO: 2 given in the sequence listing, but does not have significant reactivity to any one of the peptides represented by SEQ ID NOs: 3 to 8 given in the sequence listing.

7. The antibody according to any one of the preceding aspects 1 to 6, wherein the reactivity to the peptide represented by SEQ ID NO: 2 given in the sequence listing is at least five times stronger than the reactivity to VWF purified from human plasma.

8. The antibody according to any one of the preceding aspects 1 to 7, wherein the reactivity to the peptide represented by SEQ ID NO: 2 given in the sequence listing is at least three times stronger than the reactivity to a peptide having the sequence represented by SEQ ID NO: 1 given in the sequence listing.

9. The antibody according to any one of the preceding aspects 1 to 8, wherein the reactivity to the peptide represented by SEQ ID NO: 2 given in the sequence listing is at least five times stronger than the reactivity to the peptide represented by SEQ ID NO: 8 given in the sequence listing.

10. The antibody according to any one of the preceding aspects 1 to 9, wherein a peptide which has the amino acid sequence represented by SEQ ID NO: 9 given in the sequence listing at its C-terminus is used as an immunogen to provide the antibody.

11. The antibody according to any one of the preceding aspects 1 to 10, wherein a peptide which has the amino acid sequence represented by SEQ ID NO: 2 given in the sequence listing is used as an immunogen to provide the antibody.

12. The antibody according to any one of the preceding aspects 1 to 3, wherein the antibody has reactivity to the peptide represented by SEQ ID NO: 10 given in the sequence listing.

13. The antibody according to any one of the preceding aspects 1 to 3 and 12, wherein the antibody has reactivity to a domain comprising at least 4 amino acid residues from the N-terminus of the peptide represented by SEQ ID NO: 10 given in the sequence listing.

14. The antibody according to any one of the preceding aspects 1 to 3, 12 and 13, wherein the antibody has reactivity to the peptide represented by SEQ ID NO: 10 given in the sequence listing, but does not have significant reactivity to any one of the peptides represented by SEQ ID NOs: 2 to 9 given in the sequence listing.

15. The antibody according to any one of the preceding aspects 1 to 3 and 12 to 14, wherein the reactivity to the peptide represented by SEQ ID NO: 10 given in the sequence listing is at least five times stronger than the reactivity to VWF purified from human plasma.

16. The antibody according to any one of the preceding aspects 1 to 3 and 12 to 15, wherein the reactivity to the peptide represented by SEQ ID NO: 10 given in the sequence listing is at least three times stronger than the reactivity to the peptide represented by SEQ ID NO: 1 given in the sequence listing.

17. The antibody according to any one of the preceding aspects 1 to 3 and 12 to 16, wherein the reactivity to the peptide represented by SEQ ID NO: 10 given in the sequence listing is at least five times stronger than the reactivity to the peptide represented by SEQ ID NOs: 8 or 11 given in the sequence listing.

18. The antibody according to any one of the preceding aspects 1 to 3 and 12 to 17, wherein a peptide having the amino acid sequence represented by SEQ ID NO: 12 given in the sequence listing at its N-terminus is used as an immunogen to provide the antibody.

19. The antibody according to any one of the preceding aspects 1 to 3 and 12 to 18, the peptide represented by SEQ ID NO: 10 given in the sequence listing is used as an immunogen to provide the antibody.

20. The antibody according to any one of the preceding aspects 1 to 19, wherein the antibody is a monoclonal antibody.

21. The antibody according to any one of the preceding aspects 1 to 11, wherein the antibody is a monoclonal antibody produced by a hybridoma having Accession No. FERM BP-10480 or FERM BP-10479.

22. A hybridoma producing the monoclonal antibody according to the preceding aspect 20.

23. The hybridoma according to the preceding aspect 22, wherein the hybridoma has Accession No. FERM BP-10480 or FERM BP-10479.

24. A method for measuring ADAMTS13 activity, comprising the steps of:
    reacting an ADAMTS13-cleavable substrate peptide with a sample to be assayed for an ADAMTS13 activity, and
    reacting the reaction product of the above step with at least one antibody according to any one of the preceding aspects 1 to 21.

25. A method for measuring ADAMTS13 activity of a sample, comprising the steps of:
    reacting a peptide having the sequence represented by SEQ ID NO: 1 given in the sequence listing with a sample to be assayed for an ADAMTS13 activity, and
    reacting the reaction product of the above step with at least one antibody according to any one of the preceding aspects 1 to 21.

26. A method for measuring ADAMTS13 activity of a sample comprising the steps of:

reacting VWF with a sample to be assayed for an ADAMTS13 activity, and reacting the reaction product of the above step with at least one antibody according to any one of the preceding aspects 1 to 21.

27. The method for measuring ADAMTS13 activity of a sample according to any one of the preceding aspects 24 to 26, wherein the antibody is labeled with a labeling material.

28. The method for measuring ADAMTS13 activity of a sample according to any one of the preceding aspects 24 to 27, wherein the antibody is immobilized on a solid support.

29. The method for measuring ADAMTS13 activity in a sample according to any one of the preceding aspects 24 to 28, wherein the antibody is supported on a water-insoluble particle.

30. A method for examining microangiopathic disease by the method according to any one of the preceding aspects 24 to 29.

31. A reagent or a kit comprising the antibody according to any one of the preceding aspects 1 to 21.

EFFECTS OF INVENTION

The antibody of the present invention is an antibody which specifically recognizes an antigenic determinant site produced by reacting ADAMTS13 with VWF or a peptide having the amino acid sequence represented by SEQ ID NO: 1 given in the sequence listing. Further, the antibody of interest has no significant specific reactivity to the VWF or the peptide with no affection given by ADAMTS13. The antibody of interest can be used to measure and assay ADAMTS13 enzyme activity. Namely, the antibody of the present invention can be used (1) to measure ADAMTS13 activity rapidly and easily by sandwich immunoassay and (2) to measure ADAMTS13 activity rapidly and easily by particle-labeling immunoassay, and thus the present invention has big meanings in that (3) those measurement results can be based to develop therapeutic and diagnostic drugs and the like. In addition, the antibody of the present invention can be stably produced from monocloned fused-cells, so that it has high value in industrial applicability.

DESCRIPTION OF THE PREFERRED EMBODIMENT

Figure 1:
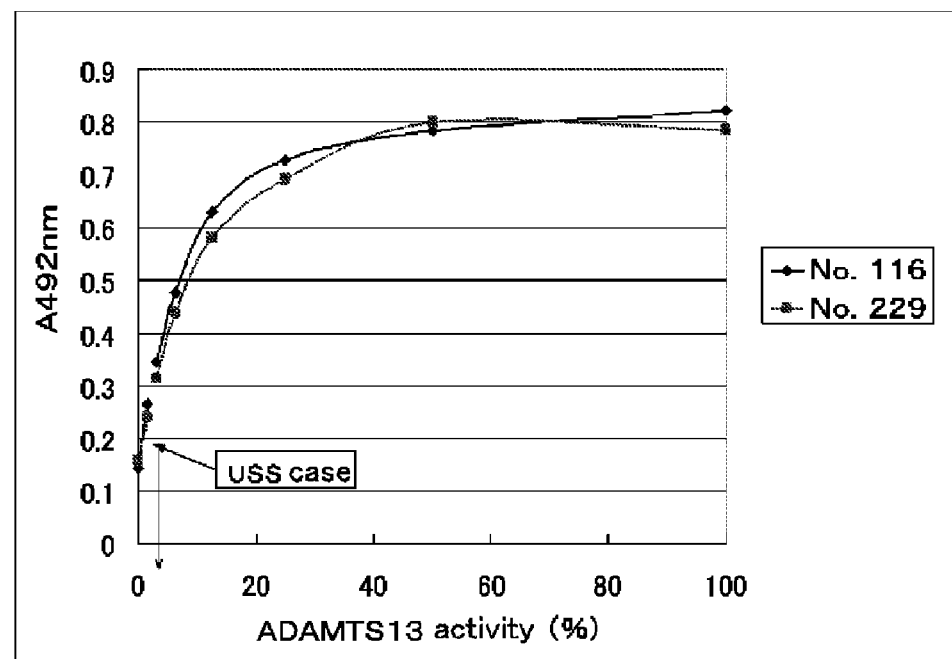
FIG. 1 shows a standard curve for measuring ADAMTS13 activity using the monoclonal antibody of the present invention as a secondary antibody and the result of measurement of USS case. (Examples 7 and 8)

In the present invention, the antibody includes both monoclonal and polyclonal antibodies. The monoclonal antibody is an antibody produced from monocloned fused-cells prepared by a well known method. The antibody of the present invention also includes both a whole antibody molecule and a moiety of the antibody molecule having the antibody activity. The antigen for use as an immunogen in producing the antibody of the present invention is not limited in particular as long as it can be served to solve the problem of the present invention, but peptides are preferably used, and the peptides of interest include those bound to carrier proteins. Further, herein "peptide" represents those formed with two or more amino acids bound by peptide bond(s).

ADAMTS13 is a zinc metalloprotease, which specifically cleaves the bond between tyrosine 1065 (Tyr1605) and methionine 1606 (Met1606) in VWF molecule. VWF is cleaved to give new C- and N-termini on the amino acid sequence. As a result, new antigenic determinant sites may be generated. Therefore, it is predicted that an antibody, which can recognize those antigenic determinant sites, is produced to be capable of specifically binding to a cleaved VWF. The antibody of the present invention is not be limited in particular as long as it has a specific reactivity to an antigenic determinant site found in a new peptide toward the N-terminal side or C-terminal side from the cleavage site. According to Nonpatent Document No. 6, it is reported that ADAMTS13 regards a peptide between Asp 1459 and Arg 1668 in VWF molecule as its substrate to cleave specifically the bond between Tyr1605-Met1606. In particular, the above literature demonstrated that a peptide composed of 73 amino acids from 1596 Asp to 1668 Arg (hereinafter referred to as "VWF73," which is the peptide represented by SEQ ID NO: 1 given in the sequence listing) is efficiently hydrolyzed by ADAMTS13. The VWF73 composed of the peptide represented by SEQ ID NO: 1 given in the sequence listing is affected by ADAMTS13 to hydrolyze between the 10th Tyr and the 11th Met, thereby to liberate a peptide composed of 10 amino acids present toward the N-terminal side from cleavage site. The peptide composed of 10 amino acids toward this N-terminal side is hereinafter also referred to as "N-10 peptide," which is a peptide having the amino acid sequence represented by SEQ ID NO: 2 given in the sequence listing.

The N-10 peptide described above could be used as an immunogen to give the antibody of the present invention which had the specific reactivity to an antigenic determinant site produced by reacting the VWF-cleaving enzyme (ADAMTS13) with von Willebrand factor (VWF) or a peptide having the amino acid sequence represented by SEQ ID NO: 1 given in the sequence listing, but did not have significant specific reactivity to VWF or the above peptide with no affection given by ADAMTS13. For the purposes herein, VWF or a peptide having the amino acid sequence represented by SEQ ID NO: 1 given in the sequence listing which has not been affected and cleaved by ADAMTS13 is usually referred to as "complete VWF molecule". Further, any peptide having the amino acid sequence represented by SEQ ID NO: 1 given in the sequence listing may serve as long as it can be hydrolyzed by ADAMTS13, and includes 73 to 2050 amino acids, preferably 73 to 210, more preferably the amino acid sequence represented by SEQ ID NO: 1 given in the sequence listing (73 amino acids).

The antibody of the present invention thus obtained recognizes an antigenic determinant site produced by reacting ADAMTS13 on VWF or a peptide having the amino acid sequence represented by SEQ ID NO: 1 given in the sequence listing and has no significant reactivity with the complete VWF molecule.

As an example of such antigenic determinant site, there may be mentioned an antigenic determinant site which is found in a peptide fragment toward the N-terminal side (peptide of SEQ ID NO: 2) produced through hydrolysis of the peptide represented by SEQ ID NO: 1 with ADAMTS. It is essential for the antigenic determinant site on the N-terminal side to contain tyrosine (Tyr) at the C-terminus. Further, the peptide of SEQ ID NO: 2 has antigenicity even if it lacks one amino acid at the N-terminus, but has no antigenicity if it lacks two amino acids. Therefore, the antigenic determinant site on the N-terminal side described above is suspected to have a folding structure composed of at least 9 amino acids.

Further, "has no significant reactivity" means that the antibody has no significant affinity for the complete VWF molecule, so that they are contacted to give no signal but the background one (a signal obtained in the absence of the antibody or a signal obtained in the presence of an irrelevant antibody to analyze), when they are analyzed to detect a signal by a known immunochemical approach such as Western blot and ELISA.

The antibody of the present invention preferably has at least one property of the following: (a) the antibody has reactivity at least five times higher with the peptide represented by SEQ ID NO: 2 given in the sequence listing than with VWF purified from human plasma, which have been immobilized on microplate wells, when the antibody is reacted with the peptide represented by SEQ ID NO: 2 given in the sequence listing or with VWF purified from human plasma, respectively; (b) the antibody has reactivity at least three times higher with the peptide represented by SEQ ID NO: 2 given in the sequence listing than with the peptide having the sequence represented by SEQ ID NO: 1 given in the sequence listing, which have been immobilized on microplate wells, when the antibody is reacted the peptide represented by SEQ ID NO: 2 given in the sequence listing or with the peptide having the sequence represented by SEQ ID NO: 1 given in the sequence listing, respectively; and (c) the antibody has reactivity at least five times higher with the peptide represented by SEQ ID NO: 2 given in the sequence listing than with the peptide having the sequence represented by SEQ ID NO: 8 given in the sequence listing, which have been immobilized on microplate wells, when the antibody is reacted with the peptide represented by SEQ ID NO: 2 given in the sequence listing or with the peptide having the sequence represented by SEQ ID NO: 8 given in the sequence listing, respectively. Alternatively, the antibody of the present invention preferably has at least one property of the following: (d) the antibody has reactivity at least five times higher with the peptide represented by SEQ ID NO: 10 given in the sequence listing than with VWF purified from human plasma, which have been immobilized on microplate wells, when the antibody is reacted with the peptide represented by SEQ ID NO: 10 given in the sequence listing or with VWF purified from human plasma, respectively; (e) the antibody has reactivity at least three times higher with the peptide represented by SEQ ID NO: 10 given in the sequence listing than with the peptide having the sequence represented by SEQ ID NO: 1 given in the sequence listing, which have been immobilized on microplate wells, when the antibody is reacted with the peptide represented by SEQ ID NO: 10 given in the sequence listing or with the peptide having the sequence represented by SEQ ID NO: 1 given in the sequence listing, respectively; and (f) the antibody has reactivity at least five times higher with the peptide represented by SEQ ID NO: 10 given in the sequence listing than with the peptides having the sequence represented by SEQ ID NO: 8 or 11 given in the sequence listing, which have been immobilized on microplate wells, when the antibody is reacted with the peptide represented by SEQ ID NO: 10 given in the sequence listing or with the peptides having the sequence represented by SEQ ID NO: 8 or 11 given in the sequence listing, respectively. These properties from (a) to (f) can be confirmed by using a method in Examples 5 through 8 described below.

When the antibody of the present invention is a monoclonal antibody, the monoclonal antibody of interest is prepared by a method as is usually employed in the art. Namely, it is produced by fusing an antibody-producing cell having an affinity specific to an antigen (for example, N-10 peptide) with a myeloma cell to form a hybridomas, which is cloned to select a clone which produce an antibody specific to each protein.

As an antigen, for example, the whole N-10 peptide, or the N-10 peptide with one to several amino acids deleted, substituted or added can be used as long as it contains at least tyrosine (Tyr) at the C-terminus and has antigenicity. It is believed that the antigenic determinant site is composed of at least 4 amino acids, and preferably 9 or more. Alternatively, the peptide having amino acid sequence represented by SEQ ID NO: 10 given in the sequence listing can be used as the antigen, or the peptide with one to several amino acids deleted, substituted or added can be used as the antigen as long as it contains at least 4 amino acids at the N-terminus of the peptide of interest and has antigenicity.

The antigen of interest can be synthesized or prepared by a genetic engineering approach based on the partial amino acid sequence selected. The obtained peptide antigen can be directly dissolved or suspended in an appropriate buffer such as phosphate buffer (PBS) to use as a sensitizing antigen. The antigen is preferably crosslinked with an appropriate carrier protein such as albumin and Keyhole Limpet Hemocyanin to obtain a stronger antigenicity. The antigen solution may usually be prepared to have a concentration of approximately between 50 and 500 µg/ml of an antigenic component. The animals to immunologically sensitize with the antigen of interest include mouse, rat, horse, goat, and rabbit. Mouse, in particular, BALB/c mouse is preferred. At that time, in order to immunize a subject animal to get enhanced response to the antigen, the antigen solution of interest can be mixed with an adjuvant to administer. As the adjuvant for use in the present invention, Freund's complete adjuvant (FCA), Freund's incomplete adjuvant (FIA), Ribi (MPL), Ribi (TDM), Ribi (MPL+TDM), *Bordetella pertussisvaccine*, muramyldipeptide (MDP), aluminum adjuvant (ALUM) and combination thereof may be exemplified. The combination with FCA at primary immunization and the combination with FIA at additional immunization are particularly preferred.

For the immunization method, injection sites, schedule and the like can be changed as appropriate in accordance with, for example, the kind of antigen to use and the presence of adjuvant to mix. For example, mice are used as the subject immunization animal to inject 0.05 to 1 ml of an antigen solution mixed with an adjuvant (10 to 200 µg of antigenic component included) intraperitoneally, subcutaneously, intramuscularly or into the (tail) vein, and additionally immunized from one to four times every about four to fourteen days after the primary immunization, and then finally immunized about one to four weeks later. The antigen solution with no adjuvant contained may be administered at an increased amount of the antigen intraperitoneally. About five to six days after the additional immunization, blood is collected to measure the antibody titer. The antibody titer can be measured by a method usually used in the art according to an antibody assay described later. On approximately the 3rd to 5th day after the last immunization, splenocytes are separated from the immunized animals to obtain antibody-producing cells.

As myeloma cells, those derived from, for example, mouse, rat and human are used. For example, as mouse myeloma cells, P3X63-Ag8, P3X63-Ag8-U1, P3NS1-Ag4, SP2/0-Ag14, P3×63-Ag8-653 and the like may be exemplified, but a same type of animal, in particular a same lineage of animal is preferably used to derive the antibody-producing cells and the myeloma cells. The myeloma cells can be cryopreserved or maintained by subculturing in a common medium supplied with the serum of horse, rabbit or fetal bovine. For fusing cells, cells in the logarithmic growth phase are preferred to use.

As the method for forming hybridomas by fusing antibody-producing cells with myeloma cells, methods using, for example, polyethylene glycol (PEG), Sendai virus and an electric fusion apparatus may be exemplified. For example, in the PEG method, splenocytes and myeloma cells may be suspended in an appropriate culture medium or buffer containing approximately from 30 to 60% PEG (having an average molecular weight of 1000 to 6000) to mix at a mixing ratio of 1-10:1, and preferably of 5-10:1, and then allowed to react for approximately 30 seconds to 3 minutes at a temperature of about 25 to 37° C. and a pH of 6 to 8. After the termination of the reaction, the cells are separated from PEG solution, suspended again in the culture medium, and seeded in cell well plates to keep culturing.

The cells subjected to fusion are cultured in a selection medium to select hybridomas. The selection medium is a medium which allows parent cell strains to die and only fused-cells to proliferate, and is usually served with the hypoxanthine-aminopterin-thymidine (HAT) medium. The hybridomas is selected firstly by substituting a part of, preferably about half of the culture medium with a fresh selection medium usually 1 to 7 days after fusion, and then substituting likewise repeatedly every several days to continue culturing. Wells are observed by microscope to confirm growing colonies.

The culture supernatants may be collected and assayed for antibody to confirm whether growing hybridomas produce the desired antibodies or not. For example, when the N-10 peptide is used as an antigen, the immobilized N-10 peptide can be supplied with the culture supernatant to react, and further supplied with a secondary antibody (such as anti-globulin, anti-IgG and anti-IgM serums) labeled with, for example, fluorescent substances, enzymes and RI to react, thereby to measure antibody titer. Wells with an appropriate antibody produced are obtained like this way. Then, the peptide represented by SEQ ID NO: 8 given in the sequence listing (hereinafter also referred to as "N-15 peptide") which has been immobilized simultaneously is supplied with the supernatant to react, thereby to measure antibody titer in the same way. The signals of the N-10 and the N-15 peptides are compared to select the N-10 peptide whose signals are at least 10 times stronger than those of the latter. Further, monoclones are separated by a method using, for example, limiting dilution, soft agar assay and fluorescence excitation cell sorter. For example, in limiting dilution, hybridoma colonies can be serially diluted with a medium to get around 1 cell/well, and cultured to isolate a clone producing the desired monoclonal antibody. The obtained antibody-producing hybridomas can be frozen with a cryoprotective agent such as approximately 10% (v/v) dimethylsulfoxide (DMSO) or glycerin to store at −70 to −196° C. for about half a year to semi-permanent period. The cells are rapidly thawed in a thermostat bath at around 37° C. before use. It is desirable to wash them well before use to prevent the cryoprotective agent from remaining to exhibit cytotoxicity.

The monoclonal antibodies of the present invention obtained by the method described above are, for example, those monoclonal antibodies which belong to IgG or IgM class derived from mice, and designated as "VWF-peptide Ab N10-116" and "VWF-peptide Ab N10-146". The subclass of antibody produced by hybridoma can be examined by culturing the hybridoma under a general condition and analyzing the class of antibody secreted in the culture supernatant by, for example, a commercially available kit made for determining antibody class or subclass.

Of the hybridomas producing monoclonal antibodies of the present invention, hybridomas VWF-peptide Ab N10-116 and VWF-peptide Ab N10-146 lines, which produce monoclonal antibodies of VWF-peptide Ab N10-116 and VWF-peptide Ab N10-146, have been separated for the first time by the present inventors, and specifically, deposited domestically at Patent Organism Depository Center in National Institute of Advanced Industrial Science and Technology (Central No. 6 1-1-1 Higasi, Tsukuba city, Ibaraki prefecture. Postal code/305-8566), which is an international depository institution based on Budapest Treaty, on Mar. 29, 2005, receiving Accession Nos. FERM P-20483 and FERM P-20482, and later deposited internationally, receiving Accession Nos. FERM BP-10479 and FERM BP-10480.

The method for obtaining the monoclonal antibody can be chosen appropriately from either collecting from mouse peritoneal fluid or cell culturing depending on the required amount, the nature of hybridoma or the like. Hybridomas capable of proliferating in a mouse peritoneal cavity can be obtained at a high concentration of several mg per milliliter from the peritoneal fluid. Hybridomas which cannot be grown in vivo may be obtained from a culture supernatant of cell culture. Cell culturing advantageously allows both less contamination with immunoglobulin and other contaminants which are present in the peritoneal cavity and easier purification, though it produces a smaller amount of antibody than that the in vivo method.

In case of obtaining monoclonal antibodies from mouse peritoneal cavity, for example, hybridomas (approximately more than $10^6$) are transplanted into the peritoneal cavities of BALB/c mice previously administered with a substance having immunosuppressive effects such as pristane (2,6,10,14-tetramethylpentadecane), to collect the accumulated peritoneal fluids about 1 to 3 weeks later. For heterologous hybridomas (for example, between mouse and rat), nude mice and radiation-treated mice are preferably used.

In order to obtain antibodies from a cell culture supernatant, a culture method such as the static culture method used for maintaining cells, the high-density culture method or the spinner flask culture method are used to culture the hybridomas of interest, thereby to get the culture supernatant containing the antibody. The serum contains other antibodies and contaminants such as albumin, and so involves itself in many inconveniences for purifying the antibody. Thus, as small amount as possible of serum is desirably added into a culture medium.

It is easy to purify the monoclonal antibodies from peritoneal fluid or culture supernatant by application of a fractionation such as the salting out method using ammonium sulfate or sodium sulfate, the polyethylene glycol method, the ethanol method, the DEAE Ion Exchange Chromatography, and the gel filtration which are conventionally known as purification methods for immunoglobulin. Further, when anti-monoclonal antibody of the present invention is mouse IgG antibody, purification by affinity chromatography using protein A-binding or antimouse immunoglobulin-binding support can be conducted and easy.

ADAMTS13 activity in a sample can be rapidly measured with the novel antibody of the present invention. VWF, which is a natural substrate for ADAMTS13, can also be used for the measurement. Further, the peptide having the amino acid sequence represented by SEQ ID NO: 1 given in the sequence listing and composed of from 73 to 2050 amino acids, preferably from 73 to 210 amino acids, and more preferably the peptide having amino acid sequence of SEQ ID NO: 1

(VWF73) can be used as a substrate. These substrates are preferably tagged with, for example, glutathione-S-transferase (GST) at the N-terminus of the substrate molecule by a genetic engineering approach before expression to prepare (hereinafter also referred to as "GST-VWF73 substrate"). Further, VWF73 labeled with an enzyme at its N-terminus, for example, VWF73 substrate labeled with horseradish peroxidase (HRP) at its N-terminus can be used. VWF73 substrate labeled with HRP can be prepared by adding several amino acids at the N-terminus of VWF73 peptide, one of which is then mutated into cysteine (Cys) to label with HRP (J. Thromb. Haemost., 4, 129-136, 2006). In the following, these VWF73 prepared for use as substrates are sometimes referred generically to as "VWF73 substrate".

The substrate of interest is reacted for a defined period with a sample for measurement of ADAMTS13 activity, to assay the fraction containing products (such as the N-10 peptide when VWF73 substrate is used as a substrate) produced in the enzyme-substrate reaction mixture. The measuring method is not limited as long as the antibody of the present invention is used. Various immunoassays usually employed in the art may be applied for the method. Such methods are not limited in particular as long as the method comprises the steps of reacting the enzyme-substrate reaction mixture with the antibody of the present invention to measure the immunoconjugate formed, and include the immunonephelometric assay which optically detects a precipitation or agglutination reaction, or the labeling immunoassay which uses an antibody labeled with a substance allowing easy separation to detect.

The labeling immunoassay includes, for example, radioimmunoassay using RI as a label for detecting immunoconjugates, enzyme immunoassay using an enzyme such as alkaline phosphatase and peroxidase and fluorescence immunoassay using a fluorescent substance. Depending on a subject to label, there may be used the direct method wherein the antibody to detect is directly labeled, the indirect method wherein an antibody of the antibody to detect, namely a secondary antibody, is labeled, and the like. If the indirect method is used and, for example, the antibody of the present invention is a mouse IgG monoclonal antibody, antimouse IgG polyclonal antibody may be used for the secondary antibody. To prepare the secondary antibody and to label the antibody with a fluorescent substance, RI, enzyme or the like, methods conventionally used in the art can be applied. Further, methods using biotin-avidin (or streptavidin) reaction can also be used for the measuring method of interest, and they are preferably selected in a measurement requiring a high sensitivity. The method of interest includes a method wherein the antibody of the present invention labeled with biotin is combined with streptavidin labeled with a fluorescent substance. In order to label the antibody of the present invention with biotin and label streptavidin with a fluorescent substance methods usually conducted in the art can be used, and, for example, the streptavidin labeled with a fluorescent substance or the like is also be commercially available.

In the present invention, polyclonal antibodies can be prepared as follows. Same antigen as for the monoclonal antibody is applied to an animal such as rabbit, goat, sheep, rat and mouse for immunization to obtain an antiserum. Because the obtained antiserum usually contains antibodies which induce nonspecific reactions, a substance such as human serum, human VWF, or VWF73, which may cause nonspecific reaction, is used to absorb them, thereby to enhance the specificity. Further, antibodies having a high specificity and suitable for the object of the present invention can also be obtained by affinity purification with the immunogen used.

The obtained antibodies can be used to measure ADAMTS13 activity as in the case of the monoclonal antibody.

The specific examples of the method for measuring ADAMTS13 activity using the antibody of the present invention will be explained below. Here, the methods for measuring ADAMTS13 activity will be disclosed wherein an monoclonal antibody which is obtained by using the N-10 peptide as immunogen (hereinafter also referred to as "anti-N-10 monoclonal antibody") is used as the antibody of the present invention, and the aforementioned GST-VWF73 substrate is used as the substrate, however the antibody and the substrate are not limited to those described above in particular as long as the antibody is an antibody of the present invention and the substrate is a peptide hydrolyzable by ADAMTS13.

1. An anti-GST antibody is immobilized on a solid support such as a microtiter plate, a tube or a magnetic particle to prepare an anti-GST antibody phase, on which GST-VWF73 substrate is fixed to prepare a solid phase. A reaction buffer and a sample are reacted with the solid phase, and then the anti-N-10 monoclonal antibody is reacted to measure the amount of the anti-N-10 monoclonal antibody trapped on the solid support, allowing measurement of ADAMTS13 activity in the sample. The anti-N-10 monoclonal antibody is preferably labeled with a widely known labeling material.

2. An anti-GST antibody is immobilized on a solid support such as a microtiter plate, a tube or a magnetic particle to prepare an anti-GST antibody phase, on which GST-VWF73 substrate is fixed to prepare a solid phase. A reaction buffer, a sample, and the anti-N-10 monoclonal antibody are simultaneously reacted with the solid phase, to measure the amount of the anti-N-10 monoclonal antibody trapped on the solid support, allowing measurement of ADAMTS13 activity in the sample. The anti-N-10 monoclonal antibody is preferably labeled with a widely known labeling material.

3. An anti-GST antibody is immobilized on a solid support such as a microtiter plate, a tube or a magnetic particle to prepare an anti-GST phase, with which the GST-VWF73 substrate, a reaction buffer and a sample are reacted, and then the anti-N-10 monoclonal antibody is reacted to measure the amount of the anti-N-10 monoclonal antibody trapped on the solid support, allowing measurement of ADAMTS13 activity in the sample. The anti-N-10 monoclonal antibody is preferably labeled with a widely known labeling material.

4. An anti-GST antibody is immobilized on a solid support such as a microtiter plate, a tubes or a magnetic particle to prepare an anti-GST phase, with which the GST-VWF73 substrate, a reaction buffer, a sample, and the anti-N-10 monoclonal antibody are simultaneously reacted to measure the amount of the anti-N-10 monoclonal antibody trapped on the solid support, allowing measurement of ADAMTS13 activity in the sample. The anti-N-10 monoclonal antibody is preferably labeled with a widely known labeling material.

5. The GST-VWF73 substrate, a reaction buffer and a sample are reacted in a container such as a test tube to prepare a reaction mixture, which is then reacted with anti-GST antibody previously immobilized on a solid support such as a microtiter plate, a tube or a magnetic particle, and then reacted with anti-N-10 monoclonal antibody to measure the amount of the anti-N-10 monoclonal antibody trapped on the solid support, allowing measurement of ADAMTS13 activity. The anti-N-10 monoclonal antibody is preferably labeled with a widely known labeling material.

6. The GST-VWF73 substrate, a reaction buffer, a sample, and anti-N-10 monoclonal antibody are reacted in a container such as a test tube to prepare a reaction mixture, which is then reacted with anti-GST antibody previously immobilized on a solid support such as a microtiter plate, a tube or a magnetic particle, to measure the amount of the anti-N-10 monoclonal antibody trapped on the solid support, allowing measurement of ADAMTS13 activity. The anti-N-10 monoclonal antibody is preferably labeled with a widely known labeling material.

7. The GST-VWF73 substrate, a reaction buffer and a sample are reacted in a container such as a test tube to prepare a reaction mixture, which is then reacted with anti-N-10 monoclonal antibody previously immobilized on a solid support such as a microtiter plate, a tube or a magnetic particle, and then reacted with anti-GST antibody to measure the amount of the anti-GST antibody trapped on the solid support, allowing measurement of ADAMTS13 activity. The anti-GST antibody is preferably labeled with a widely known labeling material.

8. The GST-VWF73 substrate, a reaction buffer, a sample, and anti-GST antibody are reacted in a container such as a test tube to prepare a reaction mixture, which is then reacted with anti-N-10 monoclonal antibody previously immobilized on a solid support such as a microtiter plate, a tube or a magnetic particle, to measure the amount of the anti-GST antibody trapped on the solid support, allowing measurement of ADAMTS13 activity. The anti-GST antibody is preferably labeled with a widely known labeling material.

9. The anti-N-10 monoclonal antibody is immobilized on a solid support such as a microtiter plate, a tubes or a magnetic particle to prepare an anti-N-10 monoclonal antibody phase, with which the GST-VWF73 substrate, a reaction buffer, and a sample are simultaneously reacted, and then an anti-GST antibody is reacted to measure the amount of the anti-GST antibody trapped on the solid support, allowing measurement of ADAMTS13 activity in the sample. The anti-GST antibody is preferably labeled with a widely known labeling material. Further, the anti-GST antibody may be previously reacted with GST-VWF73 substrate as one example of the present measurement method.

10. The anti-N-10 monoclonal antibody is immobilized on a solid support such as a microtiter plate, a tubes or a magnetic particle to prepare an anti-N-10 monoclonal antibody phase, with which the GST-VWF73 substrate, a reaction buffer, a sample, and an anti-GST antibody are simultaneously reacted to measure the amount of the anti-GST antibody trapped on the solid support, allowing measurement of ADAMTS13 activity in the sample. The anti-GST antibody is preferably labeled with a widely known labeling material. Further, the anti-GST antibody may be previously reacted with GST-VWF73 substrate as one example of the present measurement method.

11. Anti-GST antibody is immobilized on a visually or physically detectable microparticle such as a gold colloidal particle or a colored latex particle, and is reacted with the GST-VWF73 substrate, and then is supplied with a reaction buffer and a sample to conduct enzymatic reaction. Then, the reaction solution is introduced on a porous support such as a filter paper or a membrane fixed with the anti-N-10 monoclonal antibody to detect the particle such as the gold colloidal particle or the colored latex particle trapped on the porous support, allowing measurement of ADAMTS13 activity. In order to introduce the reaction solution on the porous support such as the filter paper or the membrane fixed with the anti-N-10 monoclonal antibody, the lateral flow method or the flow through method as widely known is selected to employ.

12. A reaction vessel suitable for optically detecting evanescent waves as widely known is used as a solid support, the same step as described in item 4 above is conducted, and the anti-N-10 monoclonal antibody labeled with a fluorophore appropriate for detecting evanescent waves is used to detect evanescent waves, allowing measurement of ADAMTS13 activity. Further, in this case, the intensity of evanescent waves can be measured in a time-dependent manner to rate-assay ADAMTS13 enzymatic activity. This method does not need washing and B/F separation to allow homogeneous assay.

13. Anti-GST antibody is immobilized on a gold colloidal particle, a latex particle or the like, and reacted with GST-VWF73 substrate, and then supplied with a reaction buffer and a sample to conduct enzyme reaction. Then, the reaction solution is supplied with anti-N-10 monoclonal antibody to cause agglutination reaction of particles. The agglutination can be optically or visually detected to measure the ADAMTS13 activity.

14. The GST-VWF73 substrate, a reaction buffer and a sample are reacted in a container such as a test tube to prepare a reaction solution, which is then supplied with a gold colloidal particle or a latex particle immobilized with the anti-N-10 monoclonal antibody to react, and further supplied with an anti-GST antibody, preferably an anti-GST monoclonal antibody to cause agglutination reaction of particles. The agglutination can be optically or visually detected to measure ADAMTS13 activity.

15. Human or animal VWF as a substrate is reacted with a sample to prepare a reaction solution, which can be then separated by gel electrophoresis and reacted with the antibody of the present invention to measure ADAMTS13 activity.

16. Anti-VWF antibody is immobilized on a solid support such as a microtiter plate, a tube or a magnetic particle to prepare an anti-VWF phase, on which the VWF is previously fixed to prepare a solid phase. A reaction buffer and a sample are reacted with the solid phase, and then the anti-N-10 monoclonal antibody is reacted to measure the amount of the anti-monoclonal antibody trapped on the solid support, allowing measurement of ADAMTS13 activity in the sample.

The method for measuring ADAMTS13 activity using the antibody of the present invention can be more specifically explained by the following methods. Anti-N-10 monoclonal antibody is used for the antibody of the present invention and VWF73 substrate labeled with HRP at the N-terminus as described above is used for a substrate, but the present invention is not limited to them.

1. HRP-labeled VWF73 substrate, a reaction buffer and a sample are reacted in a container such as a test tube to prepare a reaction mixture, which is then reacted with anti-N-10 monoclonal antibody previously immobilized on a solid support such as a microtiter plate, a tube or a magnetic particles, and washed to measure HRP activity on the solid support, allowing measurement of ADAMTS13 activity.

2. The anti-N-10 monoclonal antibody is immobilized on a solid support such as a microtiter plate, a tube or a magnetic particle to prepare an anti-N-10 monoclonal antibody phase, which is simultaneously supplied with HRP-labeled VWF73 substrate, a reaction buffer and a sample to react, and washed to measure HRP activity on the solid support, allowing measurement of ADAMTS13 activity.

If an antibody having the specific reactivity to the peptide represented by SEQ ID NO: 10 given in the sequence listing is used, an anti-His-tagged antibody can be used in place of the anti-GST antibody described above to conduct the similar steps. Further, different tags can be used in place of GST and His tag to conduct the above method by using substances which are able to bind specifically to their respective tags.

Samples to measure by the measuring method of the present invention are not limited in particular, and typically that is blood. This method can measure cells and tissues in level, and also measure the extracted products from the cells and the tissues as samples. The methods usually conducted in the art are applicable to these measurements.

Further, reagents or kits can contain the novel antibody of the present invention. The reagents or kits herein include those reagents or kits for measuring ADAMTS13 activity in a sample and clinical examination reagents or kits. The antibody for use herein refers to both monoclonal and polyclonal antibodies, and they are not limited as long as they can achieve the object of the present invention.

The antibody of the present invention can be applied to clinical examination which measures ADAMTS13 activity, thus the present invention covers examination methods thereof. The clinical examinations are applicable for examining risk factors in progressing states for microangiopathic diseases such as thrombotic thrombocytopenic purpura (TTP), hemolytic uremic syndrome (HUS), disseminated intravascular coagulation (DIC), cerebral infarction, chronic liver disease, malignant tumor, HIV, myocardial infarction, autoimmune disease, pregnancy complication and acute renal failure.

The present invention covers not only reagents or kits for measuring ADAMTS13 activity but also those for examination described above. These reagents or kits contain the antibody of the present invention and also VWF or a peptide applicable for a substrate, if desired. The reagents or kits can contain selected materials suitable for immunologically assaying a fraction containing the substrate for ADAMTS13 as described above and the N-10 peptide which is a product of the substrate hydrolyzed by anti-N-10 monoclonal antibody of the present invention, as appropriate. For example, for EIA method, a solid phase reagent such as microplates and magnetic particles immobilized with an antibody, a labeled-antibody reagent, a enzyme-substrate reagent, a standard solution, a wash solution, and the like can be appropriately combined to prepare a kit.

The present invention also covers, for example, the anti-N-10 monoclonal antibody prepared by using the N-10 peptide (a peptide containing a site which VWF or VWF73 is cleaved to generate on the N-terminal side), methods for measuring ADAMTS13 activity using the same, and reagents or kits therefor, as well as an antibody to a site which the substrate VWF or VWF73 is cleaved by ADAMTS13 to generate newly on the C-terminal side (a site near by the N-terminus in the peptide on the C-terminal side after cleavage). In more specifically, the antibody to a peptide represented by SEQ ID NO: 10 given in the sequence listing, the antibody which is an antibody to a peptide having the sequence shown in SEQ ID NO: 12 given in the sequence listing at the N-terminal side and shows substantially no significant reaction with full-length VWF and VWF73, the method for measuring ADAMTS13 activity using these antibodies, and the reagents or the kit containing these antibodies are also covered.

EXAMPLES

Example 1

Production of Hybridoma and Anti-N-10 Monoclonal Antibody

Method for Producing Hybridoma (1) Mouse:
7 or 8 week-old inbred BALB/c female mice were bred in an animal breeding chamber (at 23±1° C., humidity of 70%), fed with standard pellets and freed access to water.

(2) Immunization Antigen:
The N-10 peptide represented by SEQ ID NO: 2 given in the sequence listing which was chemically synthesized and chemically bound to KLH was used as an N-10 peptide antigen.

(3) Immunization Method:
The N-10 peptide antigen was prepared to have 100 µg/0.5 ml in PBS, and mixed with the same amount (0.5 ml) of Freund's complete adjuvant (supplied by Difco) to make an emulsion. 200 µl of this emulsified antigen was intraperitoneally injected to four 7 week-old female BALB/c mice respectively. Further, every two weeks, 20 µg of the antigen described above prepared to have 100 µg/ml in GERBUVANT (GERBU Biotechnik, GmbH, D-6901 Guiberg, Germany) was administered to each mouse 4 times. Further one month later, the antigen described above prepared to have 100 µg/ml in GERBUVANT was boosted as above, and then the antibody titers of the mice were measured. Additional 2 weeks later, the N-10 peptide antigen prepared to have 100 µg/ml in PBS was injecting into the tail vein of the mice having a high antibody titer for last immunization. Now, the measurement of antibody titer was conducted according to the following screening method using the serum from a mouse immunized with the antigen of interest.

(4) Cell Fusion:
Three days after the last immunization, splenectomy was conducted on the BALB/c mice and their splenocytes were suspended in DMEM culture medium to prepare splenocyte suspensions. Then, cell numbers were counted to obtain $1.9 \times 10^8$ splenocytes. A cultured myeloma cell line derived from BALB/c mouse (P3-X63-Ag8-653, hereinafter also referred to as X63 cell) which is resistant to 2-amino-6-mercaptopurine(6-thioguanine[2-amino-6-mercap topurine]) was used as a parent cell line to conduct cell fusion. The X63 cell was subcultured in DMEM culture medium (containing 5 µg/ml of 6-thioguanine) supplied with 10% fetal calf serum (FCS), and further cultured in a DMEM culture medium containing 10% FCS but not containing 6-thioguanine three days before the cell fusion, to use cells in a logarithmic growth phase. The cell number of X63 cell was counted to obtain $1.9 \times 10^8$ living cells. Polyethylene glycol-1500 was dissolved in DMEM culture medium to have a concentration of 50% (w/v), in which the splenocytes described above and X63 cells were mixed at a ratio of 1:1 to conduct cell fusion in accordance with the well known method (Kohler & Milstein, Nature, vol. 256, p. 495-497, 1975; Eur. J. Immunol. vol. 6, p. 511-519, 1976) Then, HAT selection solution containing $1 \times 10^{-4}$ M hypoxanthine, $4 \times 10^{-7}$ M amethopterin and $1.6 \times 10^{-5}$ M thymidine was added to DMEM culture medium supplied with 10% FCS and 5% BriClone (supplied by Archport) to suspend splenocytes to have $2.0 \times 10^6$ cells/ml. Then, 100 µl of this cell suspension was dispensed into each well of 96-well microtiter plates to culture in a germ-free $CO_2$ culture chamber under the condition of a temperature of 37° C., a humidity of 100% and a $CO_2$ of 5%. On day 3 after starting culture, 100 μl of HAT culture medium was added into each well, then a half of the HAT culture medium was renewed every three days to continue culturing. 2 to 3 weeks later, the desired clone producing anti-ADAMTS13 monoclonal antibody was surveyed by the following screening method of ELISA using microplates adsorbed with ADAMTS13 antigen as a solid phase.

(5) Screening:

Selection was conducted by reacting the culture supernatant of hybridoma cells described above with N-10 peptide-immobilized ELISA plates and N-15 peptide-immobilized ELISA plates to select. In this case, nonspecifically reactive clones which reacted with purified VWF and VWF73 immobilized ELISA plates were removed, while clones specifically reacting with N-10 peptide were selected. The N-10 peptide was prepared to have a concentration of 2 μg/ml, added into each well of microtiter plates by 100 μl/well, allowed to adhere overnight, washed five times with a phosphate buffer containing 0.05% Tween-20 (hereinafter abbreviated as wash solution), further blocked with a phosphate buffer containing 10% Block Ace (trade name) to prepare N-10 peptide-immobilized plates. To the immobilized plates of interest, 100 μl of the culture supernatant of the obtained hybridoma cell line described above was added, reacted at 37° C. for 60 minutes, washed five times with wash solution and further reacted at 37° C. for 60 minutes with antimouse immunoglobulin antibody (derived from goat) which had been labeled with horseradish peroxidase (hereinafter abbreviated as HRP). After the reaction, the plates were washed four times with wash solution, reacted with a substrate solution (containing 0.4 mg/ml o-phenylenediamine and 0.02% $H_2O_2$) at 37° C. for 15 minutes, then this reaction was terminated with 2N sulfuric acid to measure absorbance by an ELISA platereader at a dominant wavelength of 492 nm. A hybridoma cell line specifically reactive to ELISA plate immobilized with the N-10 peptide was selected, and cloned by limiting dilution to obtain the anti-N-10 monoclonal antibody, the VWF-peptide Ab N10-146 and the VWF-peptide Ab N10-116 respectively (hereinafter sometimes abbreviated as "N10-146" and "N10-116" respectively) using hybridomas of Accession No. FERM BP-10480 and FERM BP-10479.

Example 2

Confirmation of Specificity

N-10 and N-15 peptides were prepared to have a concentration of 2 μg/ml, added into the each well of microtiter plates by 100 μl/well, allowed to adsorb overnight, washed five times with a phosphate buffer containing 0.05% Tween-20 (hereinafter abbreviated as "wash solution"), further blocked with a phosphate buffer containing 10% Block Ace (trade name) to prepare N-10 peptide-immobilized plates and N-15 peptide-immobilized plates. To each solid plate, 100 μl of culture supernatant of each clone was added, reacted at 37° C. for 60 minutes, washed five times with wash solution and further reacted at 37° C. for 60 minutes with antimouse immunoglobulin antibody (goat derive) labeled with horseradish peroxidase (hereinafter abbreviated as "HRP"). After the reaction, the plates were washed four times with wash solution, and reacted with a substrate solution (containing 0.4 mg/ml o-phenylenediamine and 0.02% $H_2O_2$) at 37° C. for 15 minutes, and then this reaction was terminated with 2N sulfuric acid and absorbance was measured by ELISA platereader at a dominant wavelength of 492 nm.

The results are shown in Table 1.

TABLE 1

| | Absorbance (492 nm) | | | |
|---|---|---|---|---|
| Clone No. | N-10 peptide | N-15 peptide | VWF | VWF73 |
| N10-116 | 2.22 | 0.00 | 0.02 | 0.35 |
| N10-229 | 1.37 | 0.00 | 0.02 | 0.30 |
| N10-146 | 1.52 | 0.00 | 0.01 | 0.22 |

The absorbances obtained on the N-15 peptide solid support were all 0.00, while those on the N-10 peptide solid support exhibited 0.5 or more (Table 1).

Therefore, the monoclonal antibody of the present invention was turned out to be an antibody specifically recognizing the N-10 peptide in the vicinity of the C-terminus.

Example 3

Identification of Mouse Immunoglobulin Subclass

Mouse immunoglobulin subclass of the monoclonal antibody produced by the hybridoma cell line which had been obtained as a monoclone by the cloning above was determined. The mouse immunoglobulin subclass was identified by Mouse Monoclonal Antibody Isotyping kit supplied by Serotec using the culture supernatant from each hybridoma cell line. As a result, both clones VWF-peptide Ab N10-116 and VWF-peptide Ab N10-146 were proven to be IgG2.

Example 4

Confirmation of the Function of Mouse Monoclonal Antibody

VWF73 peptide expressed in *E. coli* by a well known method was fused with a tag GST at the N-terminal side and with a tag histidine 6 residue (His tag) at the C-terminal side to prepare a substrate for measuring ADAMTS13 activity (GST-VWF73 substrate). 100 μl of 1 μg/ml of the substrate was previously reacted with a microtiter plate immobilized with anti-GST antibody (derived from goat, polyclonal antibody) to prepare a solid phased substrate, to which 30 μl of normal human plasma was added to react at 37° C. for an hour. 100 μl of 5 mM Tris hydrochloride buffer (pH=8) containing 20 mM barium chloride was used as the reaction solution, because ADAMTS13 is a metalloenzyme so that it needs a divalent metal to exhibit the activity. 5 mM Tris hydrochloride buffer containing 20 mM EDTA (pH=8) in place of 20 mM barium chloride was used as the reaction solution for blind test. After the termination of the reaction, the plate was emptied of the mixture solution for enzyme-substrate reaction, washed and reacted with the anti-N-10 monoclonal antibody (clone, VWF-peptide Ab N10-146, hereinafter abbreviated as "N10-146") at 37° C. for an hour. The plate was washed to remove the anti-N-10 monoclonal antibody, reacted with antimouse immunoglobulin antibody (goat) labeled with horseradish peroxidase (HRP) at 37° C. for an hour, washed, reacted with orthophenylenediamine-hydrogen peroxide, and supplied with 1M sulfuric acid to terminate the reaction. Absorbance was measured at a wavelength of 492 nm.

The results are shown in Table 2.

TABLE 2

| Clone No. | Absorbance (492 nm) | |
| --- | --- | --- |
| | +Barium chloride | +EDTA |
| N10-116 | 0.822 | 0.20 |
| N10-229 | 0.786 | 0.20 |
| N10-146 | 0.835 | 0.05 |
| Control N15Ab | 2.58 | 2.43 |

In case of clone N15Ab used as a control, the barium chloride-containing reaction solution with enzyme reaction proceeded by ADAMTS13 and the EDTA-containing reaction solution with no reaction proceeded had an almost equal absorbance to each other in absorbance, indicating that the N-10 peptide produced by enzyme reaction with ADAMTS13 could not be measured independently from VWF73 substrate. Meanwhile, in case of anti-N-10 monoclonal antibody of the present invention (N10-146), the barium chloride-containing reaction solution with enzyme reaction proceeded by ADAMTS13 had an absorbance approximately from 14 to 63 times as high as the EDTA-containing reaction solution with no reaction proceeded. The EDTA-containing reaction solution had an absorbance of 0.2 or less in any clone (Table 2). These facts demonstrate that the anti-N-10 monoclonal antibody of the present invention has an extremely low reactivity with the VWF73 substrate, but has an extremely high specificity to react with the N-10 peptide which is produced when the substrate is enzymatically hydrolyzed by ADAMTS13. Therefore, it is clarified that the anti-N-10 monoclonal antibody of the present invention can be used to measure ADAMTS13 activity.

Example 5

Seven kinds of peptides (respectively, N-10, N-6, N-8, N-11, N-9, N-13 and N-15 peptides) represented by SEQ ID NOs: 2 to 8 given in the sequence listing were each used to prepare a solution having a concentration of 1 μg/ml, 100 μl of which was dispensed into one well of a microtiter plate, left to stand at 2 to 8° C. overnight, then washed and blocked to prepare a peptide solid phase. The peptide solid phases were each reacted with the anti-N-10 monoclonal antibody (N10-146) labeled with horseradish peroxidase (HRP) to examine the reactivity with the anti-N-10 monoclonal antibody.

The results are shown in Table 3.

TABLE 3

| | N-6 | N-8 | N-9 | N-10 | N-11 | N-13 | N-15 |
| --- | --- | --- | --- | --- | --- | --- | --- |
| Solid-phase method | 0.027 | 0.022 | 0.046 | 2.858 | 0.08 | 0.066 | 0.052 |

The N-10 monoclonal antibody exhibited the reactivity only with N-10 peptide and no significant reactivity with any other peptide. Therefore, the N-10 monoclonal antibody of the present invention was turned out to be specific to N-10 peptide, in particular to a tyrosine-containing domain at the C-terminus of N-10 peptide.

Example 6

The solutions of the peptides each prepared to have a concentration of 15.6, 31.3, 62.5, 125, 250, 500 and 1000 ng/ml were previously reacted with the anti-N-10 monoclonal antibody (N10-146) labeled with HRP and then reacted with the N-10 peptide phase so as to further confirm the above results.

The results are shown in Table 4.

TABLE 4

| Concentration of peptide added (ng/ml) | N-6 | N-8 | N-9 | N-10 | N-11 | N-13 | N-15 |
| --- | --- | --- | --- | --- | --- | --- | --- |
| 1000 | 0.785 | 0.74 | 0.721 | 0.106 | 0.7 | 0.722 | 0.889 |
| 500 | 0.831 | 0.769 | 0.692 | 0.222 | 0.744 | 0.769 | 0.756 |
| 250 | 0.791 | 0.73 | 0.826 | 0.378 | 0.767 | 0.78 | 0.737 |
| 125 | 0.786 | 0.747 | 0.739 | 0.535 | 0.75 | 0.735 | 0.747 |
| 62.5 | 0.777 | 0.747 | 0.757 | 0.66 | 0.769 | 0.799 | 0.757 |
| 31.3 | 0.821 | 0.732 | 0.754 | 0.718 | 0.775 | 0.777 | 0.773 |
| 15.6 | 0.816 | 0.754 | 0.722 | 0.759 | 0.745 | 0.727 | 0.754 |
| 0 | 0.856 | 0.811 | 0.835 | 0.869 | 0.774 | 0.767 | 0.791 |

Except for N-10 peptide, none of the peptides inhibited the reaction of the anti-N-10 monoclonal antibody with the N-10 peptide phase. Therefore, it was confirmed that the anti-N10-monoclonal antibody of the present invention was specific to N-10 peptide, in particular to a tyrosine-containing domain at the C-terminus of N-10 peptide.

Example 7

Samples were each prepared to have a dilution of ×1, ×2, ×4, ×8, ×16, ×32 and ×64 with normal human plasma which had been heated at 56° C. for 30 minutes (heated plasma), and heated plasma was also used as a sample. They were each treated as in Example 4 to make a standard curve for measuring ADAMTS13 activity wherein the normal human plasma×1 was presumed to have an ADAMTS13 activity of 100%.

The results are shown in FIG. 1. Axis X represents ADAMTS13 activity (%) and axis Y represents absorbance at 492 nm. No. 116 shows the results measured using N10-116 of the anti-N-10 monoclonal antibody. It is confirmed that the absorbance increases in proportion to ADAMTS13 activity, proving that ADAMTS13 activity can be measured by the method of the present invention.

Example 8

While the standard curve of ADAMTS13 activity was made in the same manner as in Example 4, ADAMTS13 activity in the plasma of congenital ADAMTS13 deficiency (USS case) was measured.

As a result, the USS case was calculated to have an ADAMTS13 activity of 1% or below (arrow in FIG. 1). These results were well matched the results of VWF multimer analysis. Therefore, it is revealed that the method of the present invention can specifically measure ADMTS13 activity, indicating that the method is useful for clinical examination.

Example 9

The anti-N-10 monoclonal antibody of the present invention (N10-146) was used to prepare a solution having a concentration of 1 μg/ml, each 100 μl of which was dispensed into one well of a microtiter plate and left to stand overnight to prepare an anti-N-10 antibody solid phase. 100 μl of VWF73 substrate (1 μg/ml) and 10 μl of subject plasma (prepared by diluting normal human plasma with heated plasma as in Example 7) were placed in a test tube and allowed to react at 37° C. for an hour, and then supplied with 20 μl of 50 mM EDTA to terminate the reaction respectively. 100 μl of the reactant was reacted with the anti-N-10 antibody solid phase at room temperature for an hour, washed, and then reacted with anti-GST antibody (derived from goat) labeled with HRP for an hour. Absorbance generated by enzyme reaction was measured. The normal human plasma×1 was presumed to have a subject plasma concentration (ADAMTS13 activity) of 100%.

Figure 2:
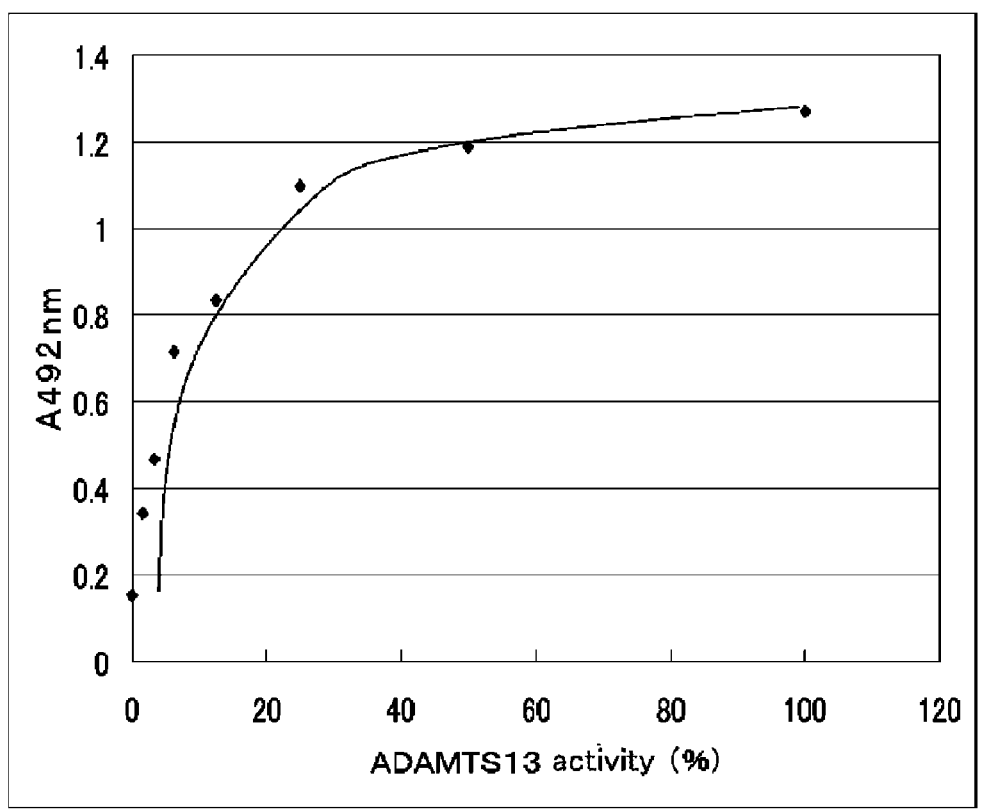
FIG. 2 shows a standard curve for measuring ADAMTS13 activity using the monoclonal antibody of the present invention for solid supports. (Example 9)

The relation between the obtained absorbance and subject plasma concentration (ADAMTS13 activity) is presented in FIG. 2. Axis X represents a subject plasma concentration (ADAMTS13 activity) (%) and axis Y represents absorbance at 492 nm. These results demonstrate that activity can be specifically measured by using the antibody of the present invention as a solid phase.

INDUSTRIAL APPLICABILITY

The anti-N-10 monoclonal antibody of the present invention is used to allow measurement and examination of activity, which can be used as a base to develop therapeutic agents, diagnostic drugs and the like.

---

The invention claimed is:

1. An isolated antibody which has the following properties: specific reactivity (affinity) to a peptide comprising at its C terminus the amino acid sequence which lacks one amino acid at the N-terminus of SEQ ID NO: 2, and significantly no specific reactivity to Von Willebrand factor (vWF) or a peptide having amino acid sequence of SEQ ID NO:1, and a peptide having amino acid sequence which lacks two amino acids at the N-terminus of SEQ ID NO: 2, wherein a signal that is obtained by reacting the antibody with vWF is the same background level of signal that is obtained without the presence of the antibody in an immunochemical assay.

2. The isolated antibody according to claim 1, wherein the antibody has reactivity to the peptide of SEQ ID NO:2.

3. The isolated antibody according to claim 1, wherein the antibody has reactivity to the peptide of SEQ ID NO: 2, but does not have significant reactivity to any one of the peptides of SEQ ID NOS:3 to 8.

4. The isolated antibody according to claim 1, wherein the antibody is a monoclonal antibody.

5. The antibody according to claim 1, wherein the antibody is a monoclonal antibody produced by a hybridoma having Accession No. FERM BP-10480 or FERM BP-10479.

6. A hybridoma producing the monoclonal antibody according to claim 4.

7. The hybridoma according to claim 6, wherein the hybridoma has Accession No. FERM BP-10480 or FERM BP-10479.

8. A reagent or a kit comprising the antibody according to claim 1.

9. A method for measuring ADAMTS13 activity, comprising the steps of:
reacting a vWF peptide having an ADAMTS13 cleavage site, and N-terminus amino acid sequence of either SEQ ID NO:2 or that lacks one amino acid at the N-terminus of SEQ ID NO: 2 with a sample to be assayed for ADAMTS13 activity to obtain a reaction product, and
reacting the reaction product of the above step with the antibody according to claim 1, and detecting the binding of the antibody with the reaction product, wherein the detection of binding indicates presence of ADAMTS13 in the sample.

10. The method according to claim 9, wherein the vWF peptide is SEQ ID NO:1.

11. The method according to claim 9, wherein the antibody has reactivity to the peptide of SEQ ID NO:2.

12. The method according to claim 9, wherein the antibody has reactivity to the peptide of SEQ ID NO: 2, but does not have significant reactivity to any one of the peptides of SEQ ID NOS:3 to 8.

13. The method according to claim 9, wherein the antibody is a monoclonal antibody.

14. The method according to claim 9, wherein the antibody is a monoclonal antibody produced by a hybridoma having Accession No. FERM BP-10480 or FERM BP-10479.

* * * * *